US010716595B1

(12) United States Patent
    Situ

(10) Patent No.: US 10,716,595 B1
(45) Date of Patent: Jul. 21, 2020

(54) FOOT EXFOLIATOR

(71) Applicant: Peter Situ, Gilbert, AZ (US)

(72) Inventor: Peter Situ, Gilbert, AZ (US)

( * ) Notice: Subject to any disclaimer, the term of this patent is extended or adjusted under 35 U.S.C. 154(b) by 182 days.

(21) Appl. No.: 15/940,859

(22) Filed: Mar. 29, 2018

Related U.S. Application Data

(60) Provisional application No. 62/479,199, filed on Mar. 30, 2017.

(51) Int. Cl.
    *A61B 17/54*     (2006.01)
    *A61B 17/32*     (2006.01)
    *A61B 17/00*     (2006.01)

(52) U.S. Cl.
    CPC ............. *A61B 17/54* (2013.01); *A61B 17/32* (2013.01); *A61B 2017/00862* (2013.01); *A61B 2017/320004* (2013.01); *A61B 2017/320012* (2013.01)

(58) Field of Classification Search
    CPC .............. A61B 17/54; A61B 17/32; A61B 2017/320004; A61B 2017/320012; A61B 2017/00761; A45D 26/0004; A45D 2200/1054
    See application file for complete search history.

(56) References Cited

U.S. PATENT DOCUMENTS

| 4,241,499 | A | * | 12/1980 | Perrone | ............... | A61B 17/54 |
| | | | | | | 132/75.4 |
| 5,621,986 | A | | 4/1997 | Medina et al. | | |
| 5,913,313 | A | * | 6/1999 | Brunderman | ......... | A61B 17/54 |
| | | | | | | 132/200 |
| 6,740,052 | B1 | | 5/2004 | Regner | | |
| 6,779,218 | B1 | * | 8/2004 | Jusinski | ............... | A46B 11/00 |
| | | | | | | 15/104.92 |
| 7,266,857 | B1 | | 9/2007 | Mezyed | | |
| 7,278,431 | B2 | | 10/2007 | Anderson et al. | | |
| 8,162,956 | B2 | | 4/2012 | Falk | | |
| 8,235,058 | B1 | * | 8/2012 | Fritts | ................... | A43B 7/00 |
| | | | | | | 132/73.5 |
| 8,545,516 | B1 | * | 10/2013 | Winnett | ............... | A61B 17/54 |
| | | | | | | 606/131 |
| 8,919,349 | B1 | * | 12/2014 | Wallace | ............... | A61B 17/54 |
| | | | | | | 132/76.5 |
| 2002/0088471 | A1 | * | 7/2002 | Sullinger | .............. | A61B 17/54 |
| | | | | | | 132/76.4 |

(Continued)

FOREIGN PATENT DOCUMENTS

| CN | 201822029 | 5/2011 |
| KR | 20130006430 | 11/2013 |

OTHER PUBLICATIONS www.amazon.com/PediSandHandsFreePersonalPedicure/dp/B019VR6FKG.
www.beachsolesusa.com/product/threebeachsoleswithsixpads/.
www.amazon.com/PersonalPedicureHandsFreeFoot/dp/B0000QRIMI/.

*Primary Examiner* — Eric J Rosen
*Assistant Examiner* — Mohammed S Adam
(74) *Attorney, Agent, or Firm* — Booth Udall Fuller, PLC

(57) ABSTRACT

A foot exfoliator may include an exfoliator base and a heel notch. The exfoliator base may include a front portion and a rear portion opposite the front portion. The heel notch may include a notch opening and a notch base, the notch opening disposed proximal to the front portion of the exfoliator base, the notch base sloping upwards from the front portion toward the rear portion, at least a portion of the notch base facing a front of the foot exfoliator.

14 Claims, 11 Drawing Sheets

(56) References Cited

U.S. PATENT DOCUMENTS

| | | | |
|---|---|---|---|
| 2004/0254587 A1* | 12/2004 | Park | A61B 17/54 606/131 |
| 2005/0216034 A1* | 9/2005 | Lind | A61B 17/54 606/131 |
| 2007/0016118 A1 | 1/2007 | Kotlizky | |
| 2007/0214557 A1* | 9/2007 | Qiu | A61B 17/54 4/286 |
| 2008/0045974 A1* | 2/2008 | Dixon | A61B 17/54 606/131 |
| 2010/0016813 A1* | 1/2010 | Brown | A61B 17/54 604/293 |
| 2010/0049211 A1* | 2/2010 | Shih | A61B 17/54 606/131 |
| 2011/0219561 A1 | 9/2011 | Tran | |
| 2012/0023694 A1 | 2/2012 | Nicas | |
| 2012/0255571 A1 | 10/2012 | Jones et al. | |
| 2015/0201969 A1* | 7/2015 | Dugo | A61B 17/54 606/131 |
| 2016/0270820 A1* | 9/2016 | Helton | A61B 17/54 |
| 2018/0353210 A1* | 12/2018 | Lipowicz | A61B 17/54 |
| 2019/0282257 A1* | 9/2019 | Roberts | A47K 3/002 |

* cited by examiner

FOOT EXFOLIATOR

RELATED APPLICATIONS

This application claims the benefit of U.S. provisional patent application 62/479,199, filed Mar. 30, 2017 titled "Foot Exfoliator," the entirety of the disclosure of which is incorporated by this reference.

TECHNICAL FIELD

Aspects of this document relate generally to foot exfoliators, and methods of using a foot exfoliator for exfoliating feet of a user.

BACKGROUND

Fewer body parts take more abuse or are exposed to more wear and tear than the feet. As a result of their near-constant use, feet often develop dry skin, cracked skin, and calluses that can be difficult and inconvenient to remove. A variety of remedies, treatments, creams, lotions, bandages, supports, and tools have become available to for the treatment and care of feet. In some instances, third parties may provide treatment, while in other instances treatment may be self-administered.

SUMMARY

According to an aspect of the disclosure, a foot exfoliator may comprise an exfoliator base, a body, a foot opening, and a heel notch. The exfoliator base may comprise a front edge, a rear edge opposite the front edge, a first side, and a second side opposite the first side, the first side and the second side extending between the front edge and the rear edge. The body may comprise an arch opposite the front edge of the exfoliator base, the body disposed above the exfoliator base and extending at least partially along the first side and the second side of the exfoliator base, a hollow space formed between the exfoliator base and the body. The foot opening may be defined by the exfoliator base and the arch of the body, providing access to the hollow space. The heel notch may comprise a notch base, the heel notch disposed proximal to the front edge of the exfoliator base (including an offset 328), the notch base forming a slope in a range of about 40°-80° with the exfoliator base.

Particular embodiments of the disclosure may comprise one or more of the following features. The heel notch may further comprise one or more heel walls, each of the one or more heel walls disposed above the exfoliator base and extending away from a notch opening. The body of the foot exfoliator may comprise a first material, and the exfoliator base may comprise a second material softer than the first material. The heel notch may have a grade of abrasiveness different from a grade of abrasiveness of a portion of the body. The notch base may comprise a first surface with a first slope and a second surface with a second slope, the first slope being greater than or less than the second slope. The exfoliator base may comprise a forefoot opening through the exfoliator base and proximal to the front edge of the exfoliator base. The notch base may be concave.

According to an aspect of the disclosure, a foot exfoliator may comprise an exfoliator base, a body, and a heel notch. The exfoliator base may comprise a front edge, a rear edge opposite the front edge, a first side, and a second side opposite the first side. The body may comprise an arch opposite the front edge of the exfoliator base, the body configured to attach to the exfoliator base at least partially along the first side and the second side of the exfoliator base, the body and the exfoliator base forming a hollow space between the exfoliator base and the body. The arch of the body and the rear edge of the exfoliator base may define a foot opening. The heel notch may comprise a notch base, the heel notch disposed on the body proximal to the front edge of the exfoliator base, the notch base forming a slope with the exfoliator base.

Particular embodiments of the disclosure may comprise one or more of the following features. The heel notch may further comprise one or more heel walls, each of the one or more heel walls disposed above the exfoliator base and extending away from a notch opening. The foot exfoliator may further comprise a brush disposed on an outer surface of the body of the foot exfoliator. The notch base may be concave. The body of the foot exfoliator may comprise an elastomeric material. The body of the foot exfoliator may comprise a first material, the exfoliator base may comprise a second material, and the foot opening may comprise a third material softer than the first material. The slope of the notch base may be in a range of about 40°-80°. The body of the foot exfoliator may comprise a first material, the exfoliator base may comprise a second material, and the foot opening may comprise a third material, the exfoliator base further comprising a forefoot opening that comprises a fourth material softer than the second material.

According to an aspect of the disclosure, a foot exfoliator may comprise an exfoliator base and a heel notch. The exfoliator base may comprise a front portion and a rear portion opposite the front portion. The heel notch may comprise a notch opening and a notch base, the notch opening disposed proximal to the front portion of the exfoliator base, the notch base sloping upwards from the front portion toward the rear portion, at least a portion of the notch base facing a front of the foot exfoliator.

Particular embodiments of the disclosure may comprise one or more of the following features. The heel notch may further comprise one or more heel walls, each of the one or more heel walls extending above the exfoliator base and extending away from the notch opening. At least one of the one or more heel walls may form a peak. The notch base may be concave. The slope may be equal to or greater than 45°.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain, and ordinary meaning to the terms be applied to the interpretation of the specification and claims.

The inventors are also aware of the normal precepts of English grammar. Thus, if a noun, term, or phrase is intended to be further characterized, specified, or narrowed in some way, such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material, or acts in support of the function. Thus, even when the claims recite a "means for performing the function of . . ." or "step for performing the function of . . . ," if the claims also recite any structure, material, or acts in support of that means or step, or to perform the recited function, it is the clear intention of the inventors not to invoke the provisions of 35 U.S.C. § 112112(f). Moreover, even if the provisions of 35 U.S.C. § 112(f), are invoked to define the claimed aspects, it is intended that these aspects not be limited only to the specific structure, material, or acts that are described in the preferred embodiments, but in addition, include any and all structures, material, or acts that perform the claimed function as described in alternative embodiments or forms in the disclosure, or that are well-known present or later-developed, equivalent structures, material, or acts for performing the claimed function.

The foregoing and other aspects, features, and advantages will be apparent to those artisans of ordinary skill in the art from the DETAILED DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DETAILED DESCRIPTION

Figure 1A:
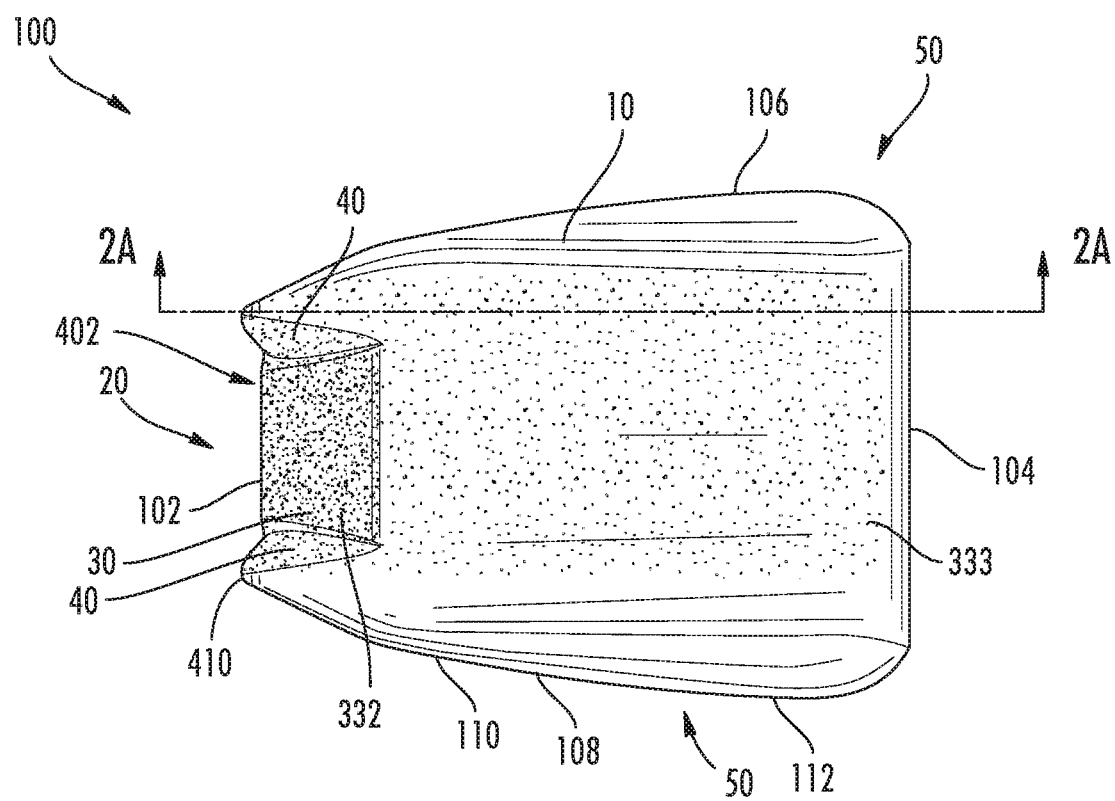
FIG. 1A is a top view of a foot exfoliator.

This disclosure, its aspects and implementations, are not limited to the specific material types, system component examples, or methods disclosed herein. Many additional components, manufacturing and assembly procedures known in the art consistent with product design and manufacture are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes embodiments in many different forms, they are shown in the drawings and will herein be described in detailed particular embodiments with the understanding that the present disclosure is to be considered as an exemplification of the principles of the disclosed methods and systems, and is not intended to limit the broad aspect of the disclosed concepts to the embodiments illustrated.

Human feet tend to develop calluses and dry cracked skin from repeated use. Conventional solutions include tools that are attached to the floor of a shower or can only be used while sitting or bending down. Attaching and detaching the tools is inconvenient, while leaving them in place can be a tripping hazard. Sitting or bending down makes it difficult to exfoliate feet while in the shower.

Figure 1B:
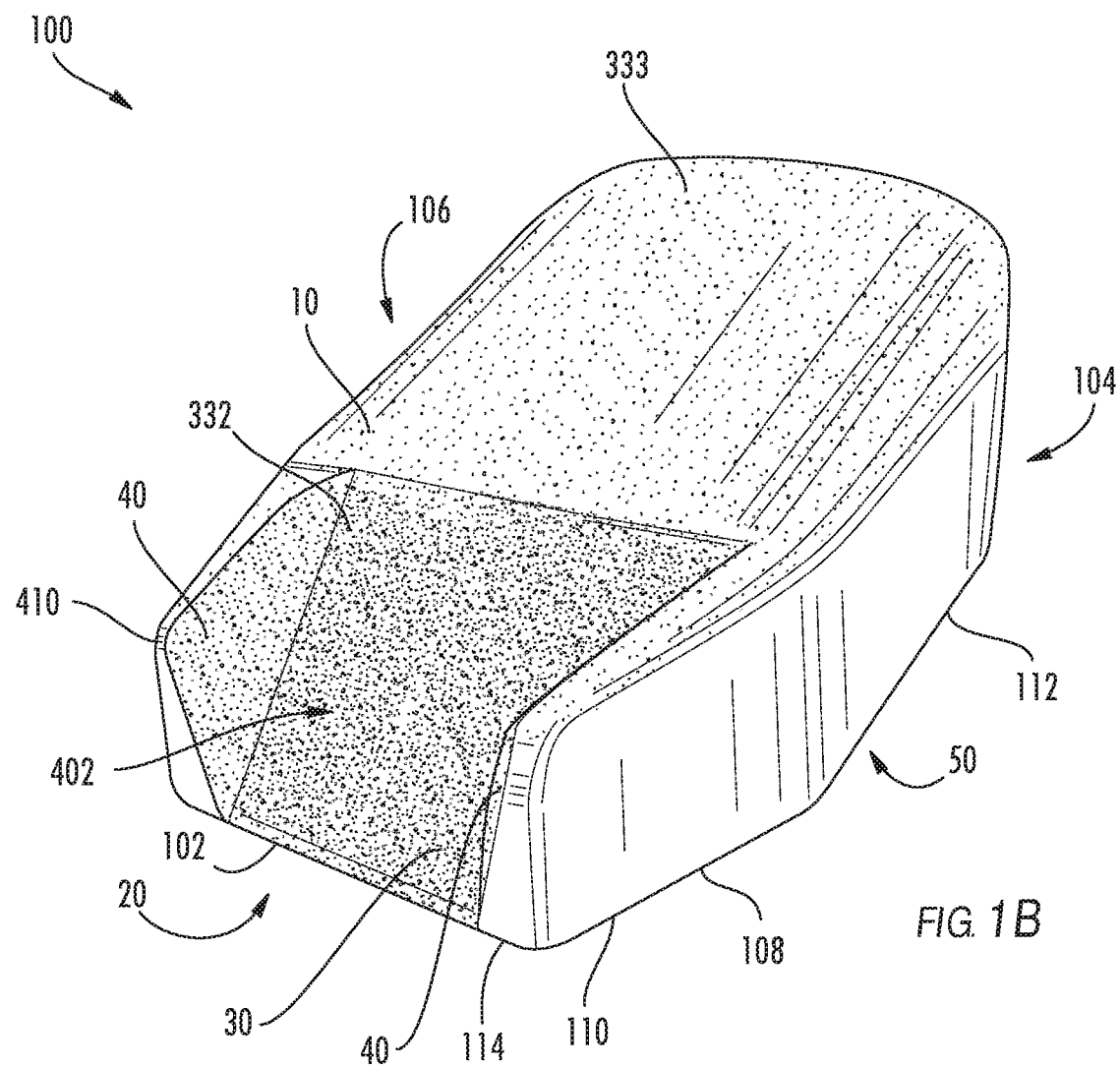
FIG. 1B is a side perspective view of the foot exfoliator shown in FIG. 1A.
Figure 1C:
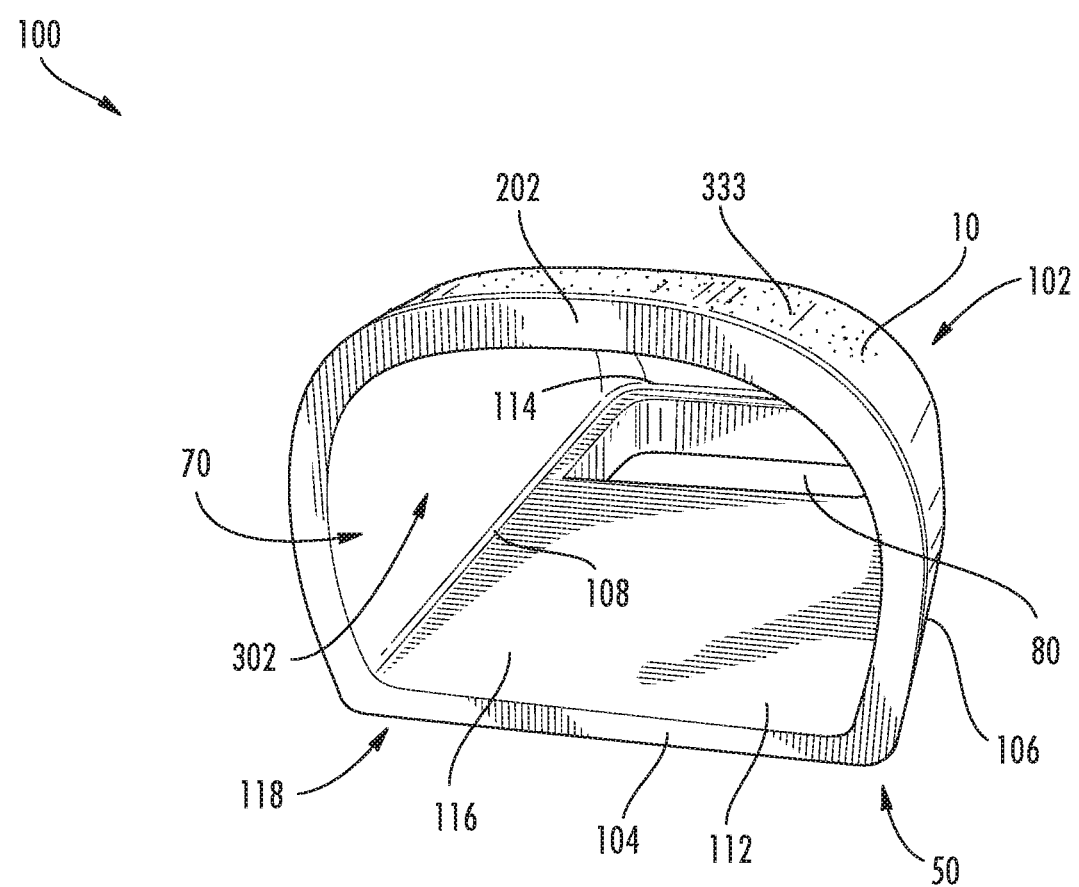
FIG. 1C is a rear view of the foot exfoliator shown in FIG. 1A.

Contemplated as part of this disclosure are foot exfoliation devices and methods of exfoliating feet in the shower hands-free. FIGS. 1A-1C show an example foot exfoliator 100. The foot exfoliator 100 may be made or formed of one or more or plastic, metal, wood, ceramic, fibers, fiberglass, carbon fibers, Kevlar, textiles, silicon, foam, stone, rubber, neoprene, or other suitable materials. In use, a user can place one foot to hold the foot exfoliator 100 in place while rubbing the other foot on the abrasive surfaces 332, 333 of the foot exfoliator 100. By using the user's bodyweight to temporarily hold the foot exfoliator 100 in place during use instead of permanently or mechanically affixing it to the floor, the device 100 is easy to deploy, reposition, and retrieve for storage. Further, the device may be used while standing, and does not require a user to use or apply force with his arms, thus providing hands free use.

An exfoliator or a foot exfoliator 100 may comprise a base or an exfoliator base 50 (FIGS. 1A-1C). The foot exfoliator 100 may further comprise a body 10. A hollow space 302 may be formed between the body 10 and the exfoliator base 50. The body 10 may comprise an arch 202. The arch 202 and the rear edge 104 of exfoliator base 50 may define a foot opening 70. In some embodiments, the rear edge extends further out than the arch of the body such that the foot exfoliator resembles a slipper. The foot opening 70 may provide access to the hollow space 302. The foot opening 70 may comprise a third material that is softer than the first material of the body 10 such that, when the foot 700 is placed through the foot opening 70 into the hollow space 302, the foot opening 70 is gentle on the top of the foot 700. The third material may comprise one or more of plastic (e.g., vinyl nitrile), cloth, silicone, foam, or any other suitable material. In some embodiments, the exfoliator base 50 and the body 10 may be formed as an integral or unitary piece while, in other embodiments, the exfoliator base 50 and the body 10 may be made of separate or distinct pieces that are separately or later assembled for use.

The exfoliator base 50 comprises a front portion 110 and a rear portion 112 opposite the front portion 110 (FIGS. 1A-2B). The exfoliator base 50 further comprises a front edge 102 at or on the front portion 110, a rear edge 104 at or on the rear portion 112, opposite the front edge 102, a first side 106, and a second side 108 opposite the first side 106. The first side 106 and the second side 108 connect the front edge 102 and the rear edge 104. The exfoliator base 50 also comprises a top 116 and a bottom 118, where the bottom 118 may contact the floor or ground, including a floor of a tub or shower, and the top 116 is opposite the bottom. The body 10 may, or may be configured or adapted, to couple to the exfoliator base 50 at the first side 106 and the second side 108. In some embodiments, the body 10 is coupled with the exfoliator base 50 as one piece or being attached with the exfoliator base 50. In some embodiments, the body 10 is detachably coupled with the exfoliator base 50 with one or mechanical or chemical fasteners, such as buckles, snaps, locks, tabs, flanges, or other mechanisms known to a person skilled in the art.

Figure 4A:
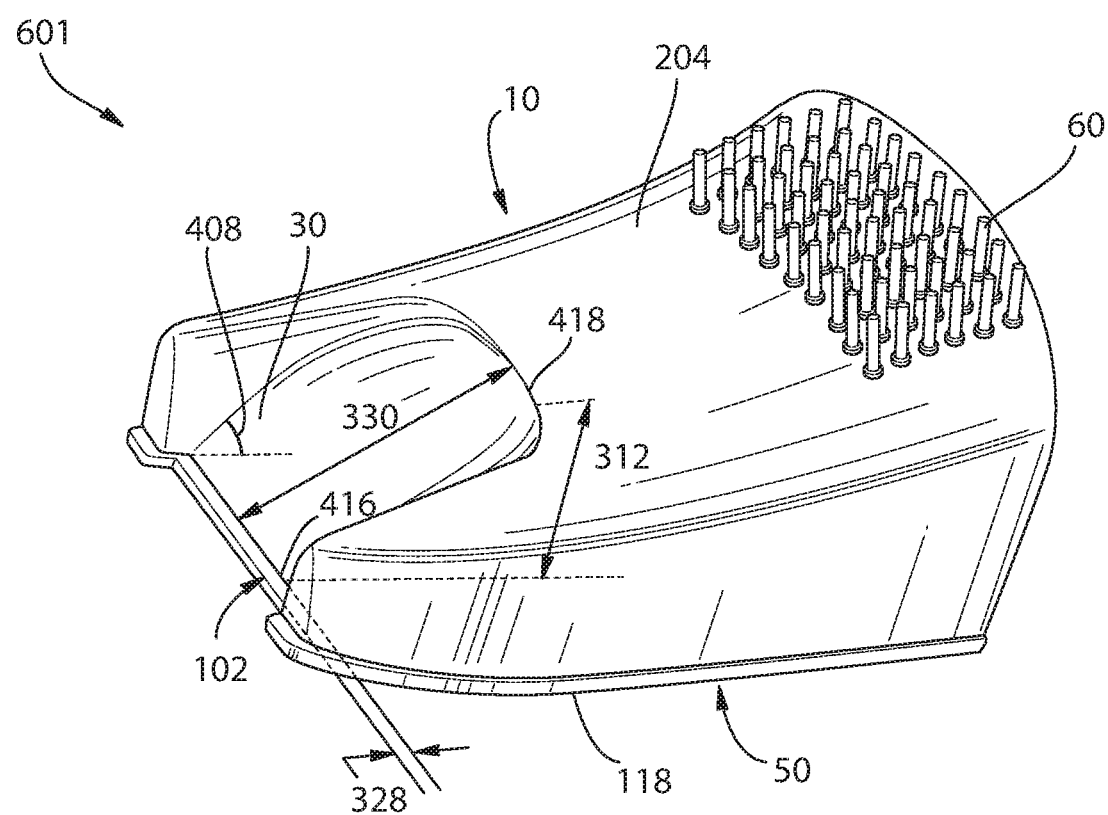
FIG. 4A shows a second example of a foot exfoliator.

The foot exfoliator 100 may further comprise a notch or a heel notch 20, as shown, for example, in FIGS. 1A, 1B, 2A, and 4A-6. The heel notch 20 may comprise a notch base 30 and a notch opening 402. At least a portion of the notch base 30 and at least a portion of the notch opening 402 face the front 114 of the exfoliator base 50. The notch base 30 may be sloped having a height 312 between the rear edge 418 of the notch base 30 and the exfoliator base 50. The length 330 of the notch base 30 may be, or may be about, 10 centimeters (cm), or in the range of about 7-20 cm or 5-15 cm (see FIG. 4A). As used herein, "substantially" or "about" will mean a value equal to a value within plus or minus (+/−) 20% or less of the stated value, +/−10% or less of the stated value, +/−5% or less of the stated value, +/−3% or less of the stated value, or +/−1% or less of the stated value. The length 330 is the distance between the front edge 416 of the notch base 30 and the rear edge 418 of the notch base 30. The notch base 30 may be planar, or substantially planar. The notch base 30 may have a curvature or be concave (see FIGS. 4A-4B). The notch base may curve inward one fifth of the height 312 of the notch base 30 (FIG. 4A). Height 312 of the notch base 30 is the distance between the rear edge 418 of the notch base 30 and the bottom 118 of the exfoliator base 50. The depth of the curved or concave notch base may be in the range of about 0.2-1 cm, 0.5-2 cm, or 0.4-1.5 cm. The heel notch 20 may be disposed on the body 10 of the foot exfoliator 100, where the notch base 30 forms a slope 408 with the exfoliator base 50. In some embodiments, the heel notch 20 is disposed on the exfoliator base 50 proximate to the front portion 110 of the exfoliator base 50 and the notch base 30 slopes upwards from the front portion 110 toward the rear portion 112 and forms a slope 408 between the notch base 30 and the bottom 118 of the exfoliator base 50. The distance 328 between the front edge 102 of the exfoliator base 50 and the front edge 416 of the notch base 30 (see FIG. 4A) may be zero (0), or located at a same position without being separated, and in other instances may be in the range of about 0.1 millimeters (mm)-1 cm, 0.01 mm-0.5 cm, or 0.2 mm-2 cm, and still be proximate. The slope 408 may start at or near the front edge 102 of the exfoliator base 50 (FIGS. 1A-1B) or at or near the front edge 416 of the notch base 30 (FIGS. 4A-4B). As used herein, near means about 2 cm or less, 1 cm or less, 5 mm or less, 2 mm or less, or 1 mm or less.

The heel notch 20 may further comprise one or more notch walls 40 extending above the exfoliator base 50 and away from the notch opening 402. The notch base 30 may be bordered by the notch walls 40. In some embodiments, the notch base may not bordered by the notch walls, but may instead be bordered by, or be adjacent with, a gap, opening, or channel disposed between the notch walls 40 and the edges of the notch base 30.

A source of difficulty in caring for the skin of the feet is that calluses and dry skin may form on a myriad of surfaces which are at many different angles. The heel, in particular, can develop rough skin on surfaces with many different angles. The heel notch 20 of the foot exfoliator 100 may be used to smooth parts of the heel that may be otherwise hard to reach, especially when the person whose heal needs exfoliating is standing, and even when sitting.

Figure 4B:
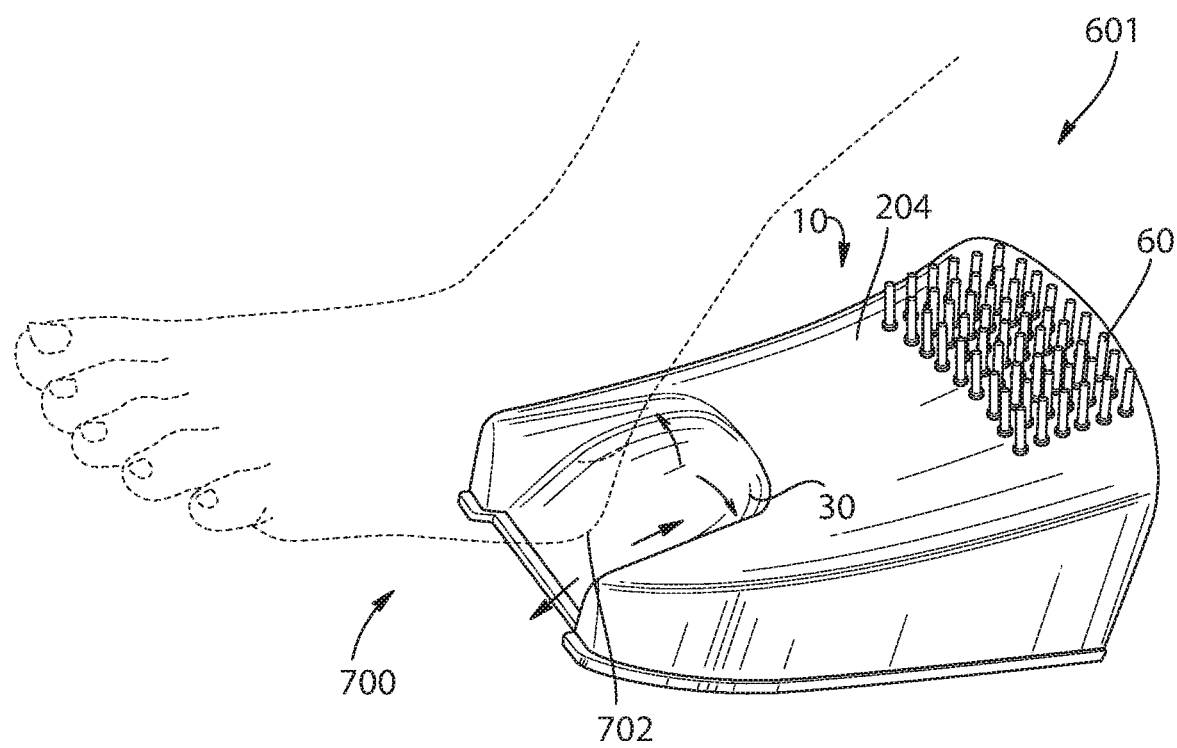
FIG. 4B shows using the foot exfoliator of FIG. 4A to exfoliate a foot.
Figure 5:
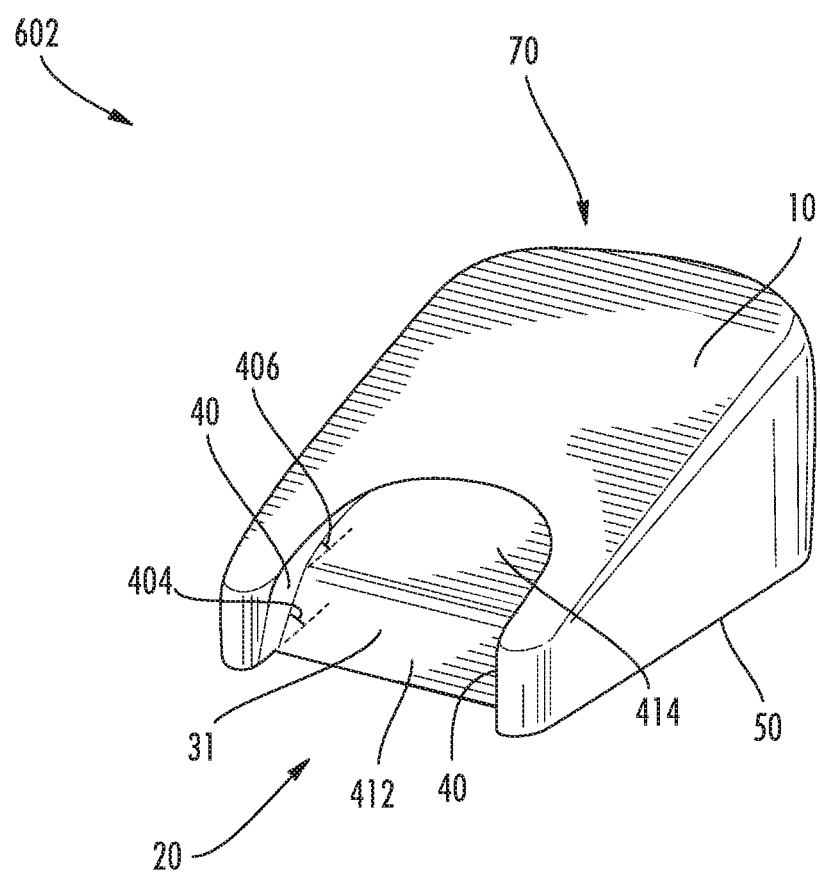
FIG. 5 shows a third example of a foot exfoliator.
Figure 6:
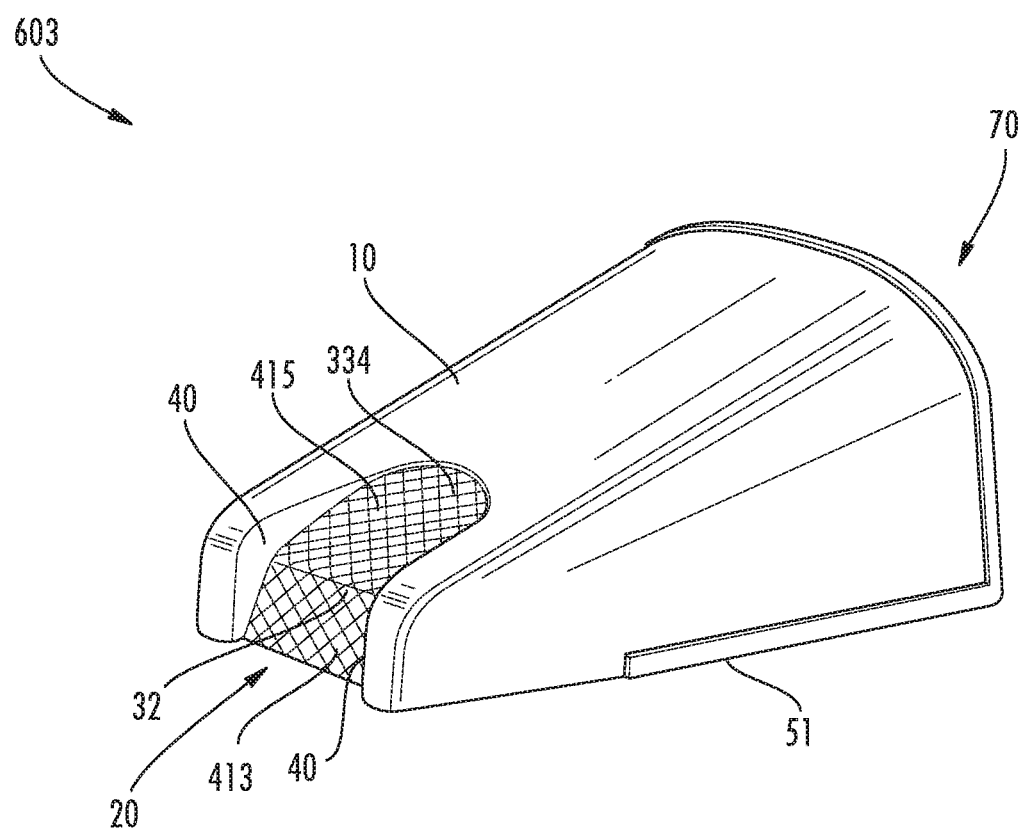
FIG. 6 shows a fourth example of a foot exfoliator.

To solve the problem of exfoliating skin on the feet, especially the heels, at many different angles, the notch base 30 may be angled or sloped at a slope 408 (see, e.g., FIGS. 1A-1C, 2A, and 4A-6). The slope of the notch base or the slope of a surface on the notch base 30 may be defined as the angle between the surface formed by the notch base 30 or the surface on the notch base 30 and the bottom 118 of the exfoliator base 50. FIGS. 1A-1C and 4A-4B show embodiments in which the heel notch 20 comprises a notch base 30 with one sloped surface for exfoliating the foot 700, especially the heel of the user. The slope 408 may start at the front edge 102 of the exfoliator base 50, or the front edge may extend further forward of the starting point of the slope. In some embodiments, the notch base 30 may comprise multiple surfaces, or may be curved, to broaden the number of sloped surfaces available to a user (FIGS. 5 and 6). In some embodiments, the notch base 31, 32 of the foot exfoliator 602, 603 comprise a first surface 412, 413 having a first slope 404 and a second surface 414, 415 having a second slope 406. The first slope 404 may be different from the second slope 406. The first and second surfaces 412, 414 may be connected with each other. In some embodiments, the first and second surfaces are disjointed from each other. Multiple surfaces allow a user to conveniently reach multiple parts of the foot 700 or the heel 702. Because the notch base 30 is sloped, the part of the heel toward the ankle can be reached and exfoliated. The slope of the exfoliator base may be about 45°. The slope may be equal to or greater than 35°, 40°, 45°, 55° or 65°. The slope may be in the range of 45°-55°, 40°-80°, 40°-50°, 35°-65°, or 45°-85°.

The heel notch 20 may further comprise one or more notch walls 40 (FIGS. 1A-1B). The notch wall may form a peak 410 at its end or along its upper edge. The peaks 410 may be used to smooth surfaces of a user's toes and areas between the toes. The notch walls 40 may meet the notch base 30 at an angle, to assist with the smoothing of surfaces of the foot 700, including between and around toes of the foot 200. In some embodiments, the notch walls 40 may meet the notch base 30 at a right angle, or other suitable angles. In some embodiments, the notch walls 40 may be at a roughly 90° angle to the exfoliator base 50.

Figure 2A:
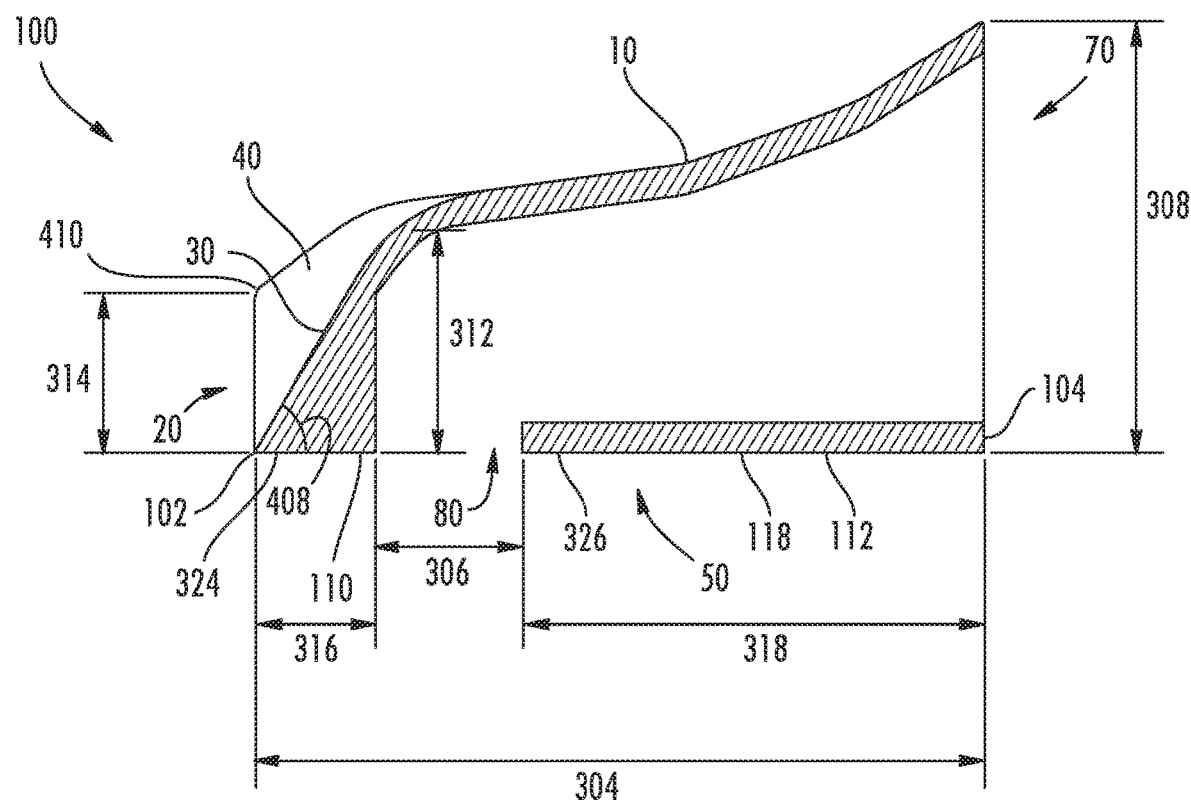
FIG. 2A shows a cross section of the foot exfoliator shown in FIG. 1A, along the section line 2A-2A.
Figure 2B:
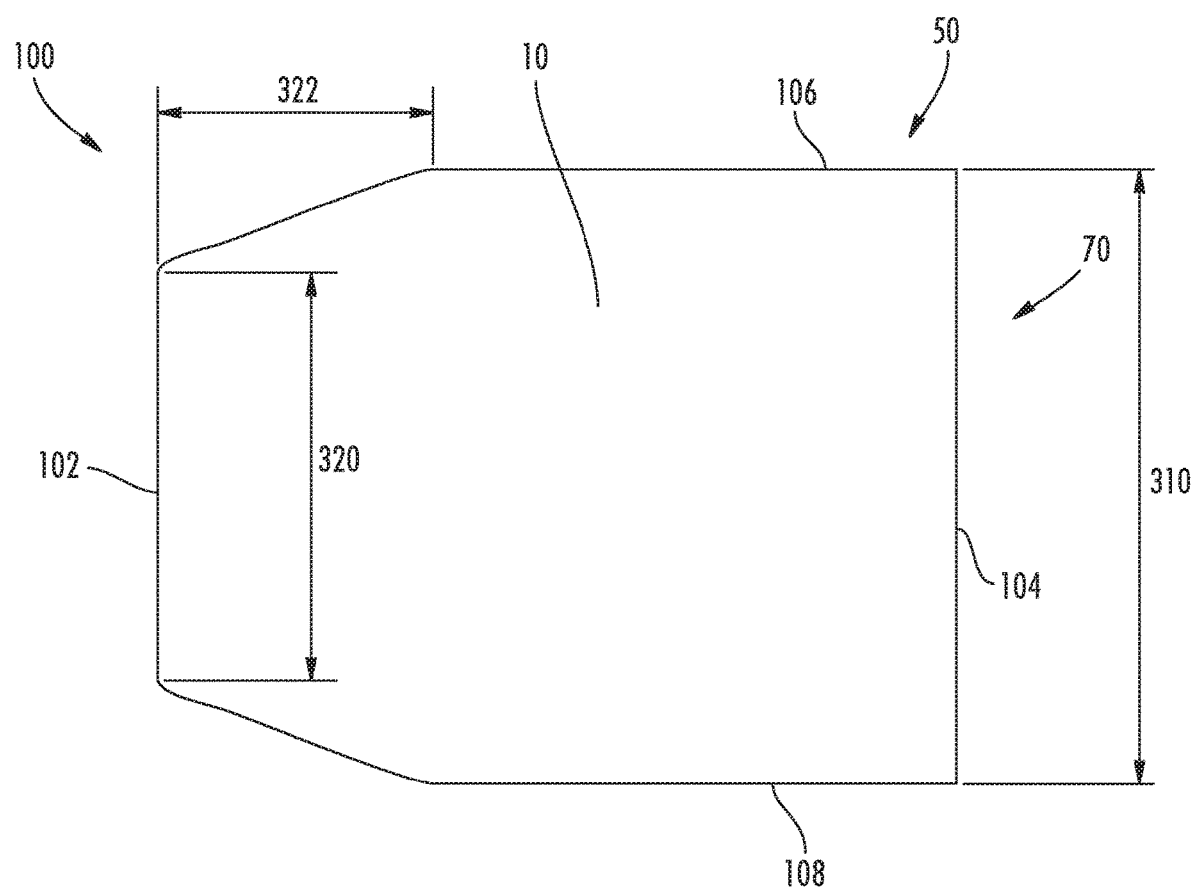
FIG. 2B is the top outline of the foot exfoliator shown in FIG. 1A.

The exfoliator may be sized to allow the foot 700 to fit into the hollow space 302 of the foot exfoliator 100 or to comfortably place one foot (a free foot) on the notch base while the other foot 700 (an anchor foot) holds the exfoliator base. FIGS. 2A and 2B show exemplary or possible dimensions for a foot exfoliator 100, and range of dimensions being "about" or "substantially" equal to the recited values.

FIG. 2A shows a cross sectional side or elevation view of the foot exfoliator 100 taken along section line 2A-2A, as indicated in FIG. 1A. FIG. 2B shows an outline, footprint, silhouette, or plan view of the foot exfoliator 100 from FIG. 1A, as viewed from above. As shown in FIG. 2B, the foot exfoliator 100 may taper down toward the toes of the anchor foot or toward the front or front edge 102 of the foot exfoliator 100 from a greater height to a lesser height. The length 322 of the tapered portion of the foot exfoliator 100 may be about 5.715 cm (2¼ inches (in.)). The foot exfoliator 100 may comprise an overall length 304 in a range of about 10.16-30.48 cm, about 12.7-20.32 cm, or about 15.875 cm (4-12 in., 5-8 in., or 6¼ in., respectively). The overall length of the foot exfoliator 100 may be the length from the farthest point to the front of the foot exfoliator to the farthest point to the rear of the foot exfoliator 100. The forefoot opening 80 may separate the exfoliator base 50 into a first portion 324 and a second portion 326. The length 316 of the first portion 324 of the exfoliator base 50 may be about 2.54 cm (1 in.). The length 318 of the second portion 326 of the exfoliator base 50 may be about 5.08-22.86 cm, about 7.62-15.24 cm, or about 10.16 cm (2-9 in., 3-6 in., or about 4 in., respectively). The width 320 of the heel notch 20 may be about 7.62-10.16 cm or about 7.94 cm (3-4 in. or 3⅛ in., respectively). The height 312 of the notch base 30 may be about 2.54-5.08 cm or about 3.97 cm (1-2 in. or 1%6 in, respectively). The height 308 of the foot opening 70 may comprise a height in a range of about 7.62-12.7 cm or about 7.94 cm (3-5 in. or 3⅛ in., respectively). The width 310 of the foot opening 70 may be about 7.62-17.78 cm, about 10.16-12.7 cm or about 12.22 cm (3-7 in., 4-5 in. or 4¹³⁄₁₆ in., respectively). The height 314 of the notch wall 40 from the bottom 118 of the exfoliator base 50 may be about 2.54-7.62 cm or about 3.33 cm (1-3 in., or 1⁵⁄₁₆ in., respectively).

In some embodiments, the foot exfoliator 100 may further comprise a forefoot opening 80 through the exfoliator base 50. The forefoot opening 80 may be disposed proximal to the front edge 102 of the exfoliator base 50. The forefoot opening 80 may be sized or configured to receive the toes, the ball, or the forefoot of the foot 700 of a user. Through the forefoot opening 80, the ball or the forefoot of the user's anchor foot may make contact with the floor. The forefoot opening 80 may allow for water to drain through the foot exfoliator 100 when used, e.g., in the shower, and also allow for a user's toes, or the ball or forefoot of the foot 700 of the user to contact and grip a surface on which the exfoliator base 50 is resting, such as the shower floor, especially when the exfoliator base 50 is composed of a material that can slide on a wet surface. The length 306 of the forefoot opening 80 may be in the range of about 1.27-7.62 cm, about 2.54-5.08 cm, or about 3.175 cm (½-3 in., 1-2 in., or 1¼ in., respectively) (FIG. 2A). The forefoot opening 80 may comprise a fourth material that is softer than the second material that the exfoliator base 50 comprises. The fourth material may comprise one or more of silicone, cloth, plastic (e.g., vinyl nitrile), or foam. In some embodiments, the portion of the base 50 that borders the opening 80 may be composed of soft or spongy material, for the comfort of the user, even if the rest of the base 50 is composed of something harder.

In some embodiments, the foot exfoliator 601 may further comprise a brush 60 disposed on the outer surface 204 of the body 11 (FIGS. 4A-4B). The brush 60 may be used to brush away loose skin, massage the foot 700, or clean or smooth the foot 700. The brush 60 may be composed of bristles made of natural or synthetic materials, or some combination of both. In some embodiments, the brush 60 may be composed of bristles having uniform mechanical properties while, in others, the brush 60 may be softer in some places than in the other places. Other embodiments of the foot exfoliator 100, 601 may include a brush 60 disposed over varying amounts of the surface, and may include a brush disposed on the top and side surfaces of the foot exfoliator 100, 601.

While various aspects of the foot exfoliator are discussed with respect to foot exfoliator 100 and foot exfoliator 601, a person of ordinary skill in the art (POSA) will understand that the features discussed with respect to one or the other (100, 601) are also applicable to each other in any desirable combination, even if not expressly recited. For simplicity, brevity, and ease of explanation, features and variations have been discussed without expressly reciting every combination of features or every possible permutation.

According to various embodiments, the dimensions of the foot exfoliator 100, 601 may depend upon sizing and the materials with which it is made. In some instances, the foot exfoliator 100, 601 may be made as a one-size-fits-all design, or one or more of a small, medium, or large design, as well as a unisex design, or male and female designs. In one embodiment, where the body is composed of a flexible elastomeric material, the dimensions may be chosen such that the foot exfoliator has a tighter fit on an anchor foot. In some embodiments, where the body is composed of a rigid material such as wood or polycarbonate, the dimensions may be chosen such that the foot exfoliator has a looser fit, to make it compatible with a wider range of users. In other embodiments, depending upon the material used, the first and second side of the exfoliator base may provide an appropriate level of grip against a wet shower floor. The foot exfoliator may be made of materials that are durable and easily cleaned, including being dishwasher safe and being able to be sanitized in a dishwasher, autoclave, or steam sanitizer.

The body 10 and the notch base 30 of the foot exfoliator 100 may be made of materials (such as the first material and the second material), that comprise one or more of stone (including pumice), rubber, metal, wood, stone, thermoplastic (e.g. polycarbonate, nylon, and acrylonitrile butadiene styrene (ABS)), an elastomer (e.g. ethylene-vinyl acetate (EVA), EVA foam, silicon and rubber), or other suitable materials. The foot exfoliator 100, 601 may comprise components made from different or additional suitable materials. Further, the second material that forms the exfoliator base 50, 51 may be the same or different from the first material that forms the body 10. For example, the body 10 may be composed of a hard material such as polycarbonate to provide a hard surface against which a foot 700 may be rubbed, while the exfoliator base 50, 51 may be composed of a softer material such as EVA foam, to provide cushioning for the user's anchor foot 700. In some embodiments, the second material of the exfoliator base 51 may comprise a non-slip material (FIG. 6). In some embodiments, a component may be composed of multiple materials. For example, the exfoliator base 50 may be composed of a hard material such as wood for its structural and aesthetic properties, but enhanced with segments of elastomer, to prevent slipping on a wet shower floor.

Figure 3:
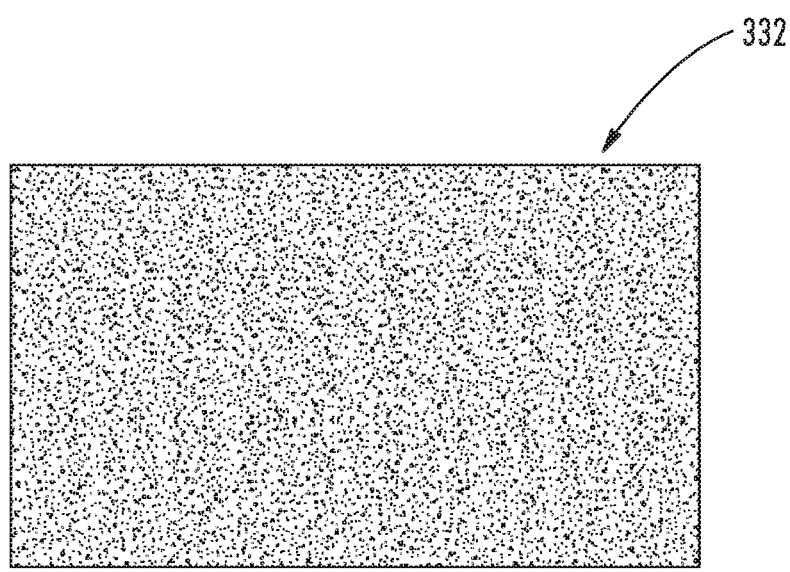
FIG. 3 shows an example of texture on a portion of the surface of the foot exfoliator shown in FIG. 1A.

To facilitate the exfoliation of the foot 700, the notch base 30 may comprise abrasive, rough, or coarse material or surface textures. The body 10 may also comprise abrasive material, textures, or patterns. FIG. 3 shows the texture of the surface of an example body 10 or an example notch base 30. The grade, grit, roughness, or of abrasiveness of the abrasive material on a portion of the body may be different from that of the material of the notch base 30, 31, 32 so that different parts of the foot 700 are exfoliated by different parts of the foot exfoliator, with different roughness of the abrasive, or both. In some embodiments, the grade of abrasiveness of the abrasive materials of the body 10 is less than that of the materials of the notch base 30. For example, the abrasive surface 332 of the notch base 30 may be more abrasive than the abrasive surface 333 on the body 10 of the exfoliator 100 (see, e.g., FIGS. 1A-1C). The forefoot and midfoot may be exfoliated by the body 10 while the heel of the foot may be exfoliated by the heel notch 20. Further, the notch walls 40 may differ from the notch base 30 in degree of abrasiveness, such as with the notch walls 40 being rougher than the notch base 30, or the notch walls 40 being smoother than the notch base 30.

The abrasive surfaces 332, 333 of a foot exfoliator 100 may also vary in density, hardness, or both, according to some embodiments (FIGS. 1A-1C). The abrasiveness of a surface, or more specifically, the effectiveness of a surface in removing material from another object, may depend upon grain size and/or shape, as well as grain density. A densely populated surface may abrade effectively, but may also quickly become bound up in the removed material. A less densely populated surface may not remove as much material for each pass, but the additional space between grains may allow for easier cleaning and more efficient use overall. The density of surface grains of the abrasive surfaces of the foot exfoliator may vary depending upon factors such as their location, orientation, and exposure to the running water when used in the shower, to facilitated washing away of removed skin.

In some embodiments, the abrasive outer surfaces may be inherent to the shape and/or material used. For example, abrasive surfaces may be created during the manufacturing process (e.g. formed by a mold). In some embodiments, abrasive surfaces may be created by removing material from the foot exfoliator 100 components after creation, to create rough surfaces.

In some embodiments, abrasive surfaces may be added to the foot exfoliator 100. For example, the abrasive surfaces 334 on a heel notch 20 may be composed of a metal such as stainless steel, nickel, or other metallic or other composite, including rust-free metals, that has been shaped to remove dry skin such as rasp-like or file-like surface, which may be seen, e.g., in FIG. 6. In some instances, the abrasive surface comprises a textured or uneven surface with varying lines and contours such as that formed at a surface of choppy water in a swimming pool or when wet paint is placed between two pieces of paper that are pulled apart. In other instances, the uneven surface may be similar to splatter texture or finish used for plaster or drywall. The abrasive surface may comprise lines, valleys, and ridges of abrasive material that may be unevenly, randomly, or stochastically formed across at least a portion of the abrasive surface, such as at or in the heel notch 20.

In some embodiments, abrasive materials (e.g. sandpaper, sanding cloth, sand, aluminum oxide, or grit) may be added to the surfaces of the foot exfoliator 100 using any of the adhering or attachment techniques known in the art, whether chemical such as using adhesives, mechanical, electrostatic or some combination of them. As an option, the grit may be sealed onto the surfaces with a coat of sealant material. In some embodiments, solid abrasive materials (e.g. stone or pumice) may be shaped complementary to, and then affixed to, various surfaces of the foot exfoliator 100. According to some embodiments, the abrasive materials and surfaces may be replaceable while, in others, they are a permanent part of the foot exfoliator 100. Of course, other embodiments may employ a variety of these techniques, and others known in the art, including any of the materials or methods used in forming the Microplane Colossal Pedicure Rasp, the Sandpaper Foot File, the Exfoliating Stone File, the Checi Foot and Nail Files (including the Nickel Callus Remover), or the Pedicure Foot File Callus Rasp Scrubber.

In use, a user would put one foot inside the foot exfoliator 100 using the foot opening 70 or, when the foot exfoliator 100 does not have a body 10 above the exfoliator base 50, a user would step on the foot exfoliator directly with the anchor foot and use the foot exfoliator 100. To smooth a heel, the user would place the heel 702 of his or her free foot 700 on the notch base 30 and rub the heel 702 against the notch base 30 (see FIG. 4B). The rubbing may be in a linear motion of rubbing up and down the notch base 30 by extending and bending his/or her free leg (see FIG. 4B). The rubbing may be in a rotational motion by twisting the ankle or rotating the foot 700 of the free leg to allow a range of surfaces of the heel to interact with the notch base 30 and the concave surface of the notch base 30, as well as the notch walls 40 (see FIG. 4B). When used in the shower, the flowing water may dispose of the skin removed by the foot exfoliator 100.

Figure 7:
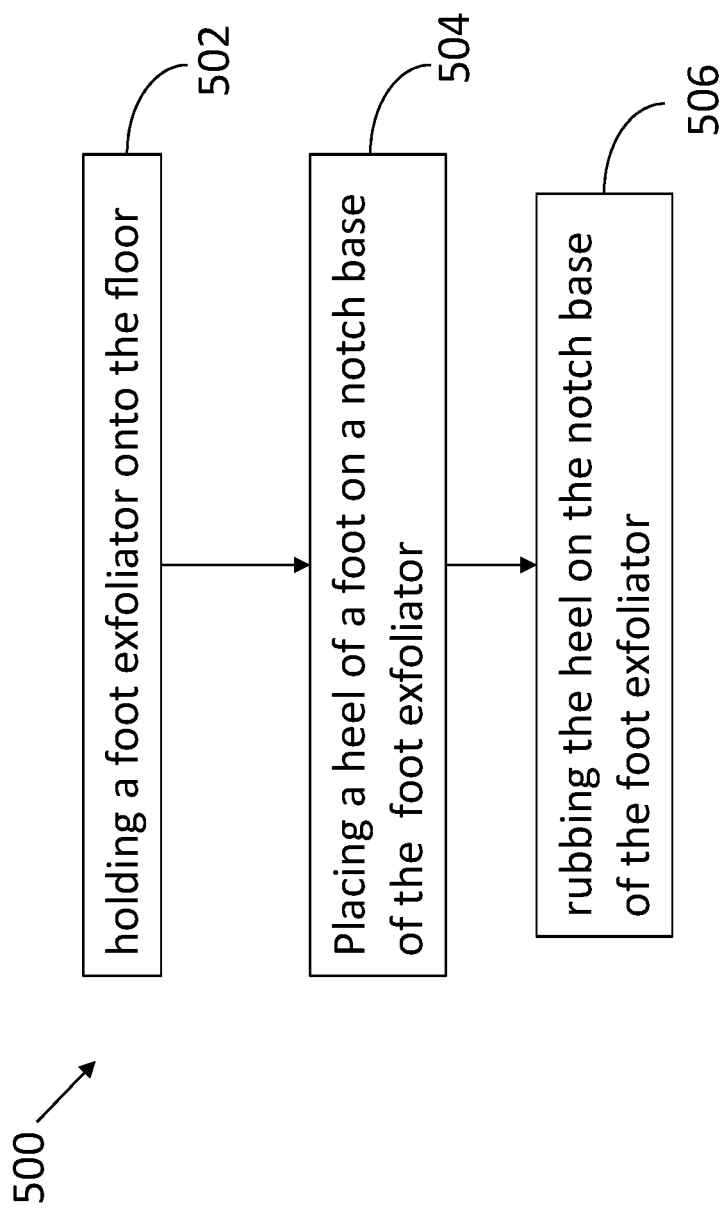
FIG. 7 is a flow chart for a method of exfoliating feet.

Methods of exfoliating feet are also provided herein. FIG. 7 illustrates an exemplary method 500. The method 500 may comprise holding a foot exfoliator onto the floor (502). The foot exfoliator may be held onto the floor by placing one foot onto the rear portion of the foot exfoliator. The foot exfoliator may also be held onto the floor by applying a force onto the rear portion of the foot exfoliator or attaching the foot exfoliator onto the floor. The method 500 further comprises placing a heel of a foot on a notch base of the foot exfoliator (504) and rubbing the heel on the notch base of the foot exfoliator (506). Rubbing the heel may be in a linear motion by going up and down the slope of the notch base or in a rotation motion by rubbing the foot against the notch wall of the notch base, the curved surface of a concave notch base, or the surface of the notch base. The method 500 may further comprise placing a notch wall of the notch base between toes and rubbing the foot against the notch wall.

When exfoliating feet with conventional solutions, a user would need to bend over or sit down, and an ideal setting for smoothing the skin on one's feet is in the shower, where hot water has softened the calluses and can wash away the resulting waste without extra steps of disposing the waste. The inconvenience of bending over, however, can be compounded by the cramped confines of a shower. Further, conventional solutions include tools that are attached to the floor of a shower, which poses as a tripping hazard and an additional hassle.

Unlike conventional exfoliating tools, a user of the foot exfoliator disclosed herein would not need to bend over or sit down. The foot exfoliator may be worn like a slipper and be held onto the floor of the shower with the anchor foot of the user, instead of being attached to the floor of the shower. Moreover, a user may use a linear or rotational motion to rub the foot of the user at various surfaces of the exfoliator to remove dried skin or calluses at the bottom of the foot, the heel of the foot, the toes, and the surfaces between the toes using one tool without significantly changing the user's position. With the foot exfoliator disclosed herein, foot exfoliating becomes less of a hassle than using a conventional tool.

This disclosure, its aspects and implementations, are not limited to the specific components or assembly procedures disclosed herein. Many additional components and assembly procedures known in the art consistent with the intended exfoliators and methods of exfoliating feet will become apparent for use with implementations of the apparatus and methods in this disclosure. In places where the description above refers to particular implementations of exfoliators, it should be readily apparent that a number of modifications may be made without departing from the spirit thereof and that these implementations may be applied to other exfoliators. The presently disclosed implementations are, therefore, to be considered in all respects as illustrative and not restrictive, the scope of the disclosure being indicated by the appended claims rather than the foregoing description. All changes that come within the meaning of, and range of equivalency of, the description are intended to be embraced therein. Accordingly, for example, although particular exfoliators and methods of exfoliating feet are disclosed, such apparatus, methods, and implementing components may comprise any shape, size, style, type, model, version, class, grade, measurement, concentration, material, quantity, or the like as is known in the art for such apparatus, methods, and implementing components, and/or the like consistent with the intended operation of the exfoliator and methods of exfoliating feet may be used.

The invention claimed is:

1. A foot exfoliator comprising:
an exfoliator base comprising a front edge, a rear edge opposite the front edge, a first side, and a second side opposite the first side, the first side and the second side extending between the front edge and the rear edge;
wherein the exfoliator base further comprises a forefoot opening through the exfoliator base and proximal to the front edge of the exfoliator base, the forefoot opening configured to allow a forefoot or toes of a user to grip a surface on which the exfoliator base is disposed and further allows water to drain through the foot exfoliator;
a body comprising an arch opposite the front edge of the exfoliator base, the body disposed above the exfoliator base and extending at least partially along the first side and the second side of the exfoliator base, a hollow space formed between the exfoliator base and the body configured to receive a first foot of a user for holding the foot exfoliator to the surface upon which the foot exfoliator is disposed;
a foot opening defined by the exfoliator base and the arch of the body and providing access to the hollow space for the first foot of the user; and
a heel notch disposed proximal to the front edge of the exfoliator base, the heel notch comprising:
a first heel wall extending along the first side of the exfoliator base,
a second heel wall extending along the second side of the exfoliator base, the second heel wall parallel to the first heel wall, and
a notch base disposed between the first heel wall and the second heel wall and forming a slope in a range of 40°-80° with the exfoliator base configured to facilitate translational movement of a heel of a second foot of the user along the notch base and away from the foot exfoliator in a direction of the first heel wall and the second heel wall.

2. The foot exfoliator of claim 1, wherein the body of the foot exfoliator comprises a first material, and the exfoliator base comprises a second material softer than the first material.

3. The foot exfoliator of claim 1, wherein the heel notch has a grade of abrasiveness different from a grade of abrasiveness of a portion of the body.

4. The foot exfoliator of claim 1, wherein the notch base comprises a first surface with a first slope and a second surface with a second slope, the first slope being greater than or less than the second slope, the first slope and second slope being configured to facilitate translational movement of the foot heel along different slopes while moving through a single direction of the translational movement.

5. The foot exfoliator of claim 1, wherein the notch base is concave.

6. A foot exfoliator comprising:
an exfoliator base comprising a front edge, a rear edge opposite the front edge, a first side, and a second side opposite the first side;
a body comprising an arch opposite the front edge of the exfoliator base, the body configured to attach to the exfoliator base at least partially along the first side and the second side of the exfoliator base, the body and the exfoliator base forming a hollow space between the exfoliator base and the body, wherein the arch of the body and the rear edge of the exfoliator base define a foot opening;
wherein the exfoliator base further comprises a forefoot opening through the exfoliator base and proximal to the front edge of the exfoliator base, the forefoot opening configured to allow a forefoot or toes of a user to grip a surface on which the exfoliator base is disposed and further allows water to drain through the foot exfoliator; and
a heel notch comprising a notch base, the heel notch disposed on the body proximal to the front edge of the exfoliator base, the notch base forming a slope with the exfoliator base.

7. The foot exfoliator of claim 6, wherein the heel notch further comprises a first heel wall and a second heel wall disposed above the exfoliator base and extending away from a notch opening, wherein the first heel wall is parallel to the second heel wall.

8. The foot exfoliator of claim 7, wherein: the heel notch is disposed above the exfoliator base and extends away from the notch opening; the first heel wall extends along the first side of the exfoliator base, and the second heel wall extends along the second side of the exfoliator base.

9. The foot exfoliator of claim 8, wherein the notch base disposed between the first heel wall and the second heel wall forms a slope in a range of 40°-80° with the exfoliator base configured to facilitate translational movement of a heel of the user along the notch base and away from the foot exfoliator in a direction of the first heel wall and the second heel wall.

10. The foot exfoliator of claim 6, further comprising a brush disposed on an outer surface of the body of the foot exfoliator.

11. The foot exfoliator of claim 6, wherein the notch base is concave.

12. The foot exfoliator of claim 6, wherein the body of the foot exfoliator comprises an elastomeric material.

13. The foot exfoliator of claim 6, wherein the body of the foot exfoliator comprises a first material, the exfoliator base comprises a second material, and the foot opening comprises a third material softer than the first material.

14. The foot exfoliator of claim 6, wherein the body of the foot exfoliator comprises a first material, the exfoliator base comprises a second material, the foot opening comprises a third material, the forefoot opening comprises a fourth material softer than the second material.

\* \* \* \* \*